US010656103B2

United States Patent
Sano et al.

(10) Patent No.: US 10,656,103 B2
(45) Date of Patent: May 19, 2020

(54) X-RAY PHASE IMAGING APPARATUS

(71) Applicant: Shimadzu Corporation, Kyoto (JP)

(72) Inventors: Satoshi Sano, Uji (JP); Taro Shirai, Osaka (JP); Takahiro Doki, Kizugawa (JP); Akira Horiba, Uji (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 296 days.

(21) Appl. No.: 15/704,345

(22) Filed: Sep. 14, 2017

(65) Prior Publication Data

US 2018/0172607 A1 Jun. 21, 2018

(30) Foreign Application Priority Data

Dec. 20, 2016 (JP) ................................. 2016-246689

(51) Int. Cl.
*G01N 23/046* (2018.01)
*G21K 1/06* (2006.01)
(Continued)

(52) U.S. Cl.
CPC ......... *G01N 23/046* (2013.01); *A61B 6/4035* (2013.01); *A61B 6/4291* (2013.01);
(Continued)

(58) Field of Classification Search
CPC .. G01N 23/046; G01N 23/041; G01N 23/207; G01N 2223/419; A61B 6/4291; A61B 6/4035; A61B 6/4429; A61B 6/42; A61B 6/40; A61B 6/06; G21K 1/067; G21K 2207/005
See application file for complete search history.

(56) References Cited

U.S. PATENT DOCUMENTS

2010/0220832 A1* 9/2010 Ning ............... A61B 6/032
378/4
2012/0183123 A1* 7/2012 Tada ............... G01N 23/046
378/62
(Continued)

FOREIGN PATENT DOCUMENTS

JP 2012-016370 A 1/2012
JP 2012125343 A 7/2012
(Continued)

OTHER PUBLICATIONS

Notice of Reasons for Refusal dated Nov. 19, 2019 for corresponding Japanese Patent Application No. 2016-246689, submitted with a machine translation.

*Primary Examiner* — Michael C Bryant
(74) *Attorney, Agent, or Firm* — Muir Patent Law, PLLC

(57) ABSTRACT

The X-ray phase imaging apparatus is configured to include an image generation unit that generates an X-ray phase-contrast image based on a phase-contrast between a step curve representing an intensity change of an X-ray when an object is placed between an X-ray source and a phase grating or between a phase grating and an absorption grating and a step curve when no object is placed therebetween, and is configured to obtain a displacement amount of relative positions of a plurality of gratings based on a plurality of step curves.

11 Claims, 8 Drawing Sheets

(51) Int. Cl.
    *G01N 23/207* (2018.01)
    *G01N 23/041* (2018.01)
    *A61B 6/00* (2006.01)
(52) U.S. Cl.
    CPC ......... *G01N 23/041* (2018.02); *G01N 23/207* (2013.01); *G21K 1/067* (2013.01); *G01N 2223/419* (2013.01); *G21K 2207/005* (2013.01)

(56) References Cited

U.S. PATENT DOCUMENTS

| | | | | |
|---|---|---|---|---|
| 2013/0083893 | A1* | 4/2013 | Ishii | A61B 6/484 378/62 |
| 2014/0205057 | A1* | 7/2014 | Koehler | G01N 23/046 378/5 |
| 2015/0320372 | A1* | 11/2015 | Sato | G01N 23/20075 378/98.12 |

FOREIGN PATENT DOCUMENTS

| | | | |
|---|---|---|---|
| JP | 2013013651 | A | 1/2013 |
| JP | 2015522157 | A | 8/2015 |
| JP | 2015524727 | A | 8/2015 |

* cited by examiner (First Embodiment)

X-RAY PHASE IMAGING APPARATUS

CROSS-REFERENCE TO RELATED APPLICATIONS

The present application claims priority to Japanese Patent Application No. 2016-246689, entitled "X-ray Phase Imaging Apparatus", filed on Dec. 20, 2016, and invented by Satoshi Sano, Taro Shirai, Takahiro Doki, and Akira Horiba, the disclosure of which is incorporated by reference in its entirety.

FIELD OF THE INVENTION

The present invention relates to an X-ray phase imaging apparatus.

BACKGROUND TECHNIQUE

Conventionally, an X-ray imaging apparatus (X-ray phase imaging apparatus) for imaging an inside of an object utilizing a phase-contrast of an X-ray that passed through the object is known. Such an X-ray imaging apparatus is disclosed, for example, in Japanese Unexamined Patent Application Publication No. 2012-16370.

The X-ray imaging apparatus disclosed in the aforementioned Japanese Unexamined Patent Application Publication No. 2012-16370 includes an X-ray source, an X-ray image detector (detection unit) arranged in the irradiation direction of the X-ray source, and a plurality of gratings arranged between the X-ray source and the X-ray image detector. In the X-ray imaging apparatus disclosed in the aforementioned Japanese Unexamined Patent Application Publication No. 2012-16370, by interfering the X-ray irradiated from the X-ray source using a plural of gratings while moving any one of the plurality of gratings in the direction of the grating pitch, the intensity-modulated signal representing the intensity change of the X-ray detected by the X-ray image detector is obtained. In the X-ray imaging apparatus disclosed in the aforementioned Japanese Unexamined Patent Application Publication No. 2012-16370, it is configured to generate a phase differential image (image) in which the inside of the object is imaged based on the phase-contrast between the intensity-modulated signal when no object is placed between the plurality of gratings and the intensity-modulated signal when an object is placed therebetween. In the X-ray imaging apparatus of this kind, it is possible to image light element bodies or soft biological tissues which are less likely to absorb an X-ray by imaging the inside of the object using not the absorption amount of the X-ray but the phase-contrast of the X-ray.

However, in the X-ray imaging apparatus as disclosed in the aforementioned Japanese Unexamined Patent Application Publication No. 2012-16370, a positional displacement of the grating from a predetermined position may sometimes occur in accordance with fluctuations of the shape and size of the member (grating stage) that supports the grating due to the influence of, e.g., heat generated at around the apparatus. In this case, in cases where there is a time difference between acquisition of the intensity-modulated signal when no object is placed between a plurality of gratings and acquisition of the intensity-modulated signal when an object is placed between the plurality of gratings, positional displacements of the gratings due to heat influence occur at the position of the grating at the time of acquiring respective intensity-modulated signals. For this reason, the intensity-modulated signal for generating the phase differential image is entirely offset. This offset can be corrected during the generating process of the phase differential image. However, when the magnitude of this offset becomes, for example, near the half period of the phase of the intensity-modulated signal, a phase-contrast caused by the object is added in addition to the offset in the vicinity of the edge portion of the object. Phase folding (phase wrapping) occurs in which the phase-contrast between an intensity-modulated signal when no object is placed between the plurality of gratings and an intensity-modulated signal when the object is placed between the plurality of gratings is folded in the range of $2\pi$. When this phase folding occurs, for example, even if the phase-contrast due to the object is $(3/2)\pi$, it cannot be distinguished from the case where the phase-contrast is $-(1/2)\pi$, which results in an erroneous measured value. As described above, in the X-ray imaging apparatus as disclosed in the aforementioned patent document, there is a problem that phase folding occurs in the phase differential image due to positional displacements of gratings caused by the influence of heat. In the present invention, the intensity-modulated signal is a concept representing an intensity change of an X-ray detected in an X-ray image detector when any one of a plurality of gratings is moved (stepped) by a distance corresponding to one cycle of a grating in a direction of a grating pitch with respect to an interference fringe formed by interfering an X-ray irradiated from an X-ray source by using a plurality of gratings.

SUMMARY OF THE INVENTION

The present invention was made to solve the aforementioned problems, and an object of the present invention is to provide an X-ray phase imaging apparatus capable of suppressing an occurrence of phase folding in an image due to a positional displacement of a grating.

In order to attain the aforementioned object, an X-ray phase imaging apparatus according to a first aspect of the present invention includes:

an X-ray source;

a plurality of gratings including at least a first grating to which an X-ray from the X-ray source is irradiated and a second grating to which the X-ray that passed through the first grating is irradiated;

a detection unit configured to detect the X-ray that passed through the second grating; and an image generation unit configured to generate an image based on a phase-contrast between an intensity-modulated signal representing an intensity change of the X-ray detected by the detection unit when an object is placed between the X-ray source and the first grating or between the first grating and the second grating and an intensity-modulated signal when no object is disposed therebetween, wherein a displacement amount of relative positions of a plurality of gratings is obtained based on a plurality of the intensity-modulated signals.

In the X-ray phase imaging apparatus according to the first aspect of the present invention, as described above, it is configured such that the displacement amount of relative positions of the plurality of gratings is acquired based on the plurality of intensity-modulated signals. With this, even if a displacement occurs in the relative positions of the plurality of gratings, the accumulation of the displacement amount can be suppressed by appropriately correcting the displacement amount. As a result, by correcting the displacement amount before the phase-contrast between the plurality of intensity-modulated signals approaches close to it, it is possible to suppress an occurrence of phase folding in the image due to a positional displacement of the grating.

In the X-ray phase imaging apparatus according to the first aspect, it is preferably configured such that the displacement amount is obtained based on a representative value obtained from the intensity-modulated signals in a region or an entire region of a plurality of pixels detected by the detection unit. With this configuration, for example, by acquiring the displacement amount by using an average value or a median value of the phase-contrast between the plurality of intensity-modulated signals in the region or the entire region of the plurality of pixels as a representative value, it is possible to acquire the displacement amount with less error. As a result, the correction of the displacement amount can be performed with high accuracy.

In the X-ray phase imaging apparatus according to the first aspect, it is preferable that the region of the plurality of pixels be a region not including an edge portion of the object. With this configuration, since it is not affected by the phase-contrast due to the presence or absence of the object, it is possible to acquire the displacement amount with less error. As a result, the correction of the displacement amount can be performed more accurately.

In the X-ray phase imaging apparatus according to the first aspect, it is preferably configured such that the displacement amount be corrected when the displacement amount exceeds a preset threshold value. With this configuration, by setting a threshold value of the displacement amount so as not to occur phase folding, in the case of the relative positional displacement to the extent that phase folding does not occur, it is possible not to correct the displacement amount. As a result, since it becomes unnecessary to correct the displacement amount each time an intensity-modulated signal is acquired, it is possible to minimize the number of corrections of the displacement amount.

In the X-ray phase imaging apparatus according to the first aspect, it is preferable that the plurality of gratings further include a third grating provided between the X-ray source and the first grating. With this configuration, by micro-focusing the X-ray irradiated from the X-ray source using the third grating, it becomes unnecessary to use a micro-focus X-ray source to form a self-image of the first grating. Therefore, it becomes possible to use an X-ray source with high X-ray intensity which cannot be obtained with a micro-focus X-ray source. As a result, the intensity of the X-ray irradiated from the X-ray source increases, which can shorten the image extraction time.

In the X-ray phase imaging apparatus according to the first aspect, it is preferable to further include a moving mechanism configured to move at least any one of the plurality of gratings to change the intensity of the X-ray detected by the detection unit. With such a configuration, it is possible to easily change the relative positions of the plurality of gratings.

In the configuration in which the X-ray phase imaging apparatus includes the moving mechanism, it is preferably configured such that the moving mechanism moves at least any one of the plurality of gratings to correct the displacement amount. With this configuration, for example, in the case of moving the grating by the moving mechanism to generate an image, a moving mechanism for imaging and a moving mechanism for correcting a displacement can be used in common. Thus, the configuration of the apparatus can be simplified and the number of parts can be reduced.

In the configuration in which the X-ray phase imaging apparatus includes the moving mechanism, it is preferably configured such that the moving mechanism corrects the displacement amount by moving the grating having a maximum grating pitch among the plurality of gratings. With this configuration, since the displacement amount is proportional to the grating pitch of the grating, when correcting with wide grating of a grating pitch, the displacement amount increases as compared with the case in which correction is performed with narrow grating of a grating pitch. As a result, since the distance for moving the moving mechanism to correct the displacement amount increases, the displacement amount can be performed easily.

In the configuration in which the X-ray phase imaging apparatus includes the moving mechanism, it is preferably configured such that the displacement amount is corrected by moving the grating moved to generate the image among the plurality of gratings by the moving mechanism. With this configuration, it is sufficient to move only a specific grating among a plurality of gratings, and therefore the grating movement by the moving mechanism can be easily performed.

In the X-ray phase imaging apparatus according to the first aspect, it is preferably configured such that the X-ray phase imaging apparatus further includes a rotation mechanism configured to relatively rotate an imaging system and the object, the imaging system including the X-ray source, the plurality of gratings, and the detection unit, wherein a tomographic image of the object is captured by relative rotating the imaging system and the object by the rotation mechanism. In this way, in the case of capturing the tomographic image of the object, since the image capturing time becomes long and the relative position of the grating is likely to be displaced, the X-ray phase imaging apparatus which can suppress an occurrence of phase folding in an image is preferable.

DESCRIPTION OF PREFERRED EMBODIMENTS

Figure 1:
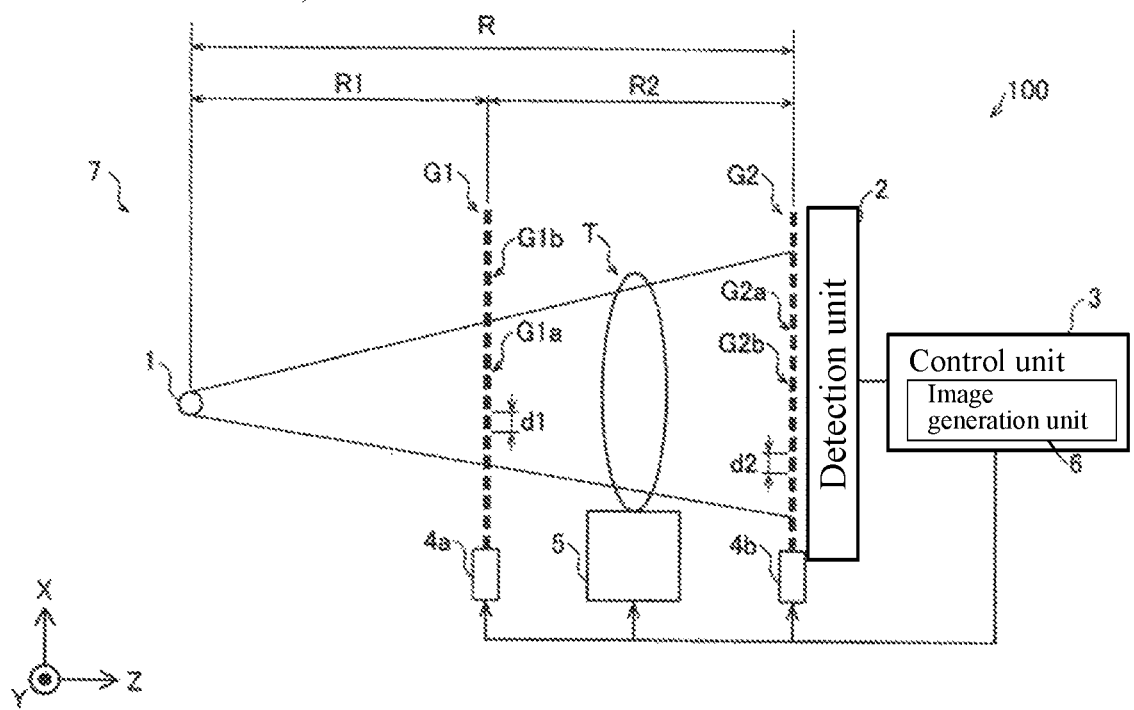
FIG. 1 is a diagram showing an overall configuration of an X-ray phase-contrast imaging apparatus according to a first embodiment of the present invention.

Hereinafter, some embodiments embodying the present invention will be described with reference to the drawings, in which various exemplary embodiments are shown. The invention may, however, be embodied in many different forms and should not be construed as limited to the exemplary embodiments set forth herein. These example exemplary embodiments are just that—examples—and many embodiments and variations are possible that do not require the details provided herein. It should also be emphasized that the disclosure provides details of alternative examples, but such listing of alternatives is not exhaustive. Furthermore, any consistency of detail between various exemplary embodiments should not be interpreted as requiring such detail—it is impracticable to list every possible variation for every feature described herein. The language of the claims should be referenced in determining the requirements of the invention.

Ordinal numbers such as "first," "second," "third," etc. may be used simply as labels of certain elements, steps, etc., to distinguish such elements, steps, etc. from one another. Terms that are not described using "first," "second," etc., in the specification, may still be referred to as "first" or "second" in a claim. In addition, a term that is referenced with a particular ordinal number (e.g., "first" in a particular claim) may be described elsewhere with a different ordinal number (e.g., "second" in the specification or another claim).

The embodiments are described, and illustrated in the drawings, in terms of functional blocks, units and/or modules. These blocks, units and/or modules may be physically implemented by electronic (or optical) circuits such as logic circuits, discrete components, microprocessors, hard-wired circuits, memory elements, wiring connections, and the like, which may be formed together in a single integrated circuit (e.g., as a single semiconductor chip) or as separate integrated circuits and/or discrete components (e.g., several semiconductor chips wired together on a printed circuit board) using semiconductor fabrication techniques and/or other manufacturing technologies. These blocks, units and/or modules may be implemented by a processor (e.g., a microprocessor, a controller, a CPU, a GPU) or processors that are programmed using software (e.g., microcode) to perform various functions discussed herein. Each block, unit and/or module may be implemented by dedicated hardware, or as a combination of dedicated hardware to perform some functions and a processor to perform other functions. Also, each block, unit and/or module of the embodiments may be embodied by physically separate circuits and need not be formed as a single integrated circuit.

First Embodiment

With reference to FIG. 1, a configuration of an X-ray phase-contrast imaging apparatus 100 according to a first embodiment of the present invention will be described. The X-ray phase-contrast imaging apparatus 100 is an example of the "X-ray phase imaging apparatus" recited in claims.

As shown in FIG. 1, the X-ray phase-contrast imaging apparatus 100 is an apparatus for imaging an inside of an object T by using the phase-contrast of the X-ray that passed through the object T. The X-ray phase-contrast imaging apparatus 100 is an apparatus for imaging the inside of the object T utilizing the Talbot effect.
(Configuration of X-Ray Phase-Contrast Imaging Apparatus)

As shown in FIG. 1, the X-ray phase-contrast imaging apparatus 100 is equipped with an X-ray source 1, a phase grating G1, an absorption grating G2, a detection unit 2, a control unit 3, grating moving stages 4a and 4b, and an object rotation stage 5. In the X-ray phase-contrast imaging apparatus 100, the X-ray source 1, the phase grating G1, the absorption grating G2, and the detection unit 2 are arranged in this order in the irradiation axis direction (optical axis direction, Z direction) of the X-ray. In this specification, the irradiation axis direction of the X-ray is defined as the Z direction, and directions orthogonal to each other in a plane orthogonal to the Z direction are defined as an X direction and a Y direction, respectively. Note that the phase grating G1 and the absorption grating G2 are examples of the "first grating" and the "second grating" recited in claims, respectively. Further, the grating moving stages 4a and 4b are examples of the "moving mechanism" recited in claims. Further, the object rotation stage 5 is an example of the "rotation mechanism" recited in claims.

The X-ray source 1 is configured to generate an X-ray when a high voltage is applied and irradiate the generated X-ray with micro-focus.

The phase grating G1 is a diffraction grating which changes the phase of the passing X-ray. The phase grating G1 has a slit G1a and an X-ray absorber G1b arranged at a predetermined period (grating pitch) d1 in the X direction. The slits G1a and X-ray absorbers G1b are each formed so as to extend in the Y direction.

The phase grating G1 is arranged between the X-ray source 1 and the absorption grating G2, and the X-ray is irradiated to the phase grating. The phase grating G1 is provided to form a self-image by a Talbot effect. When an X-ray having coherence passes through a grating in which slits are formed, a grating image (self-image) is formed at a position away from the grating by a predetermined distance (Talbot distance). This is called a Talbot effect. The self-image is an interference fringe caused by X-ray interference.

The absorption grating G2 has a plurality of slits G2a and X-ray absorbers G2b arranged at a predetermined period (grating pitch) d2 in the X direction. The slits G2a and X-ray absorbers G2b are each formed so as to extend in the Y direction.

The absorption grating G2 is arranged between the phase grating G1 and the detection unit 2, and the X-ray that passed through the phase grating G1 is irradiated to the absorption grating. Further, the absorption grating G2 is located at a position away from the phase grating G1 by the Talbot distance.

When the distance between the X-ray source 1 and the phase grating G1 is R1, the distance between the phase grating G1 and the absorption grating G2 is R2, and the distance between the X-ray source 1 and the absorption grating G2 is R (=R1+R2), the positional relationship between the X-ray source 1, the phase grating G1, and the absorption grating G2 is expressed by the following expression (1). Therefore, the grating pitch d2 of the absorption grating G2 is larger than the grating pitch d1 of the phase grating G1.

$$\frac{d2}{d1} = \frac{R}{R1} \qquad (1)$$

The detection unit 2 is configured to detect the X-ray, convert the detected X-ray into an electric signal, and read the converted electric signal as an image signal. The detection unit 2 is, for example, an FPD (Flat Panel Detector). The detection unit 2 is composed of a plurality of conversion elements (not shown) and pixel electrodes (not shown) arranged on the plurality of conversion elements. The plurality of conversion elements and pixel electrodes are arranged in the X direction and the Y direction at a predetermined period (pixel pitch).

The detection signal of the detection unit 2 is sent to the image generation unit 6 provided in the control unit 3. The image generation unit 6 is configured to generate an image including an X-ray phase-contrast image 42 (see FIG. 4) from an image obtained by placing the phase grating G1 and the absorption grating G2 at a plurality of predetermined positions. The X-ray phase-contrast image 42 is an example of the "image" recited in claims.

The control unit 3 is a computer configured by components including a CPU (Central Processing Unit), a ROM (Read Only Memory), a RAM (Random Access Memory), etc. The control unit 3 is configured to generate an image including an X-ray phase-contrast image 42 using the image generation unit 6. The control unit 3 is configured to move the phase grating G1 and the absorption grating G2 to predetermined positions using the grating moving stages 4a and 4b, respectively. The control unit 3 is provided with a storage (not shown) for storing a threshold value L, which will be described later.

The grating moving stages 4a and 4b each have a grating holding portion (not shown) for holding the phase grating G1 and the absorption grating G2. The grating moving stages 4a and 4b are each configured to move the held phase grating G1 and absorption grating G2 in prescribed directions in the Z direction, the X direction, and the Y direction based on the signal sent from the control unit 3. The grating moving stages 4a and 4b are, for example, electric positioning stages using a stepping motor or a piezo actuator. This makes it possible to easily change the relative position of the phase grating G1 and the absorption grating G2.

The object rotation stage 5 is configured so that an object T arranged between the phase grating G1 and the absorption grating G2 can be mounted thereon. Based on the signal sent from the control unit 3, the object rotation stage 5 can rotate the object T with respect to the imaging system 7 including the X-ray source 1, the phase grating G1, the absorption grating G2, and the detection unit 2 about the X axis direction or the Y axis direction as an axis by 360 degrees. The X-ray phase-contrast imaging apparatus 100 can acquire an image of the object T without using the object rotation stage 5, and also can acquire an image of the object T (acquire a CT image) at each rotation position of a predetermined rotation angle using the object rotation stage 5.

(X-Ray Phase Contrast Image Generation Method)

Next, with reference to FIGS. 2 to 5, a method of generating an X-ray phase-contrast image 42 using phase-contrast of a plurality of intensity-modulated signals will be described.

Figure 2A:
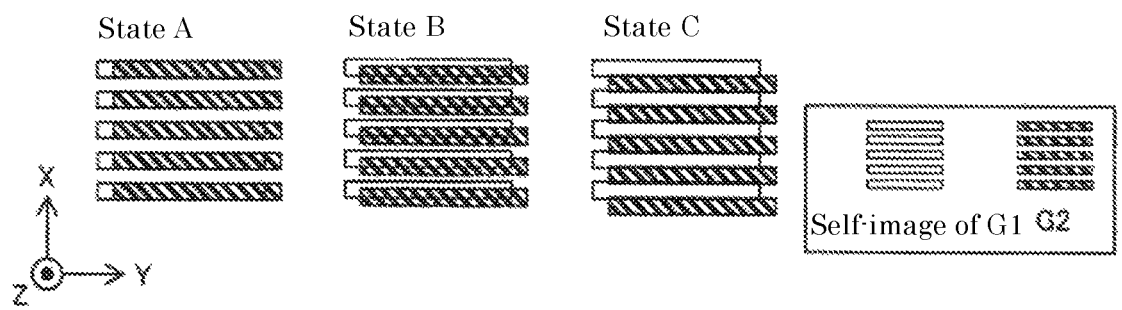
FIGS. 2A and 2B are diagrams for explaining acquisition of a step curve by a stripe manipulation.

By translating the absorption grating G2 in the pitch direction (X direction) of the grating pitch d2, the signal intensity of the X-ray detected by the detection unit 2 changes. FIG. 2A shows the changes in the overlapping degree between the self-image including the bright portion and the dark portion of the phase grating G1 and the X-ray absorber G2b of the absorption grating G2 when the absorption grating G2 is translated (stepped) in the X direction. In FIG. 2A, the state A shows a state in which the bright portion of the self-image of the phase grating G1 and the X-ray absorber G2b of the absorption grating G2 are completely overlapped. The state B shows a state in which the bright portion of the self-image of the phase grating G1 and the X-ray absorber G2b of the absorption grating G2 overlap by half. The state C shows a state in which the bright portion of the self-image of the phase grating G1 and the X-ray absorber G2b of the absorption grating G2 are completely displaced.

Figure 2B:
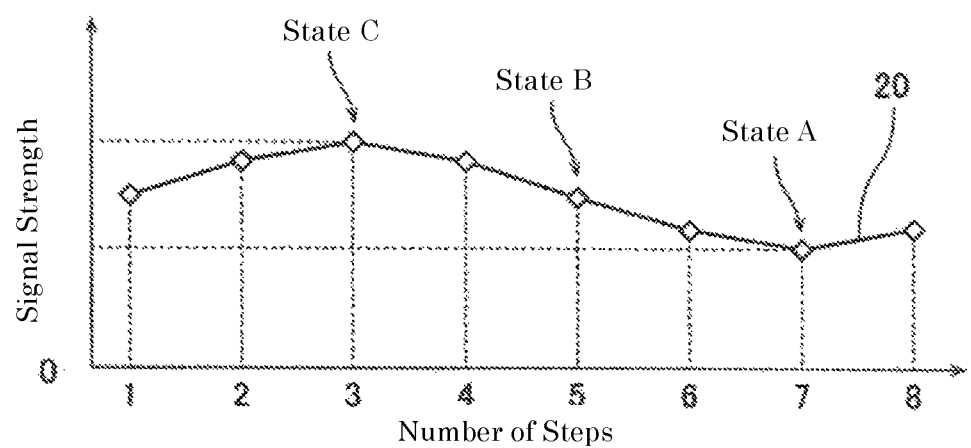

FIG. 2B shows an intensity-modulated signal 20 showing the change of the X-ray signal intensity detected by the detection unit 2 in accordance with the change in the overlapping degree between the bright portion of the self-image of the phase grating G1 and the X-ray absorber G2b of the absorption grating G2. For example, in the case of the state A shown in FIG. 2A, since the bright portion of the self-image of the phase grating G1 and the X-ray absorber G2b of the absorption grating G2 completely overlap, the amount of the X-ray that can pass through the absorption grating G2 becomes small, the signal intensity of the X-ray detected by the detection unit 2 becomes low. In the case of the state C shown in FIG. 2B, since the bright portion of the self-image of the phase grating G1 and the X-ray absorber G2b of the absorption grating G2 are completely displaced, the amount of the X-ray that can pass through the absorption grating G2 increases, the signal intensity of the X-ray detected by the detection unit 2 becomes high. In the case of the state B shown in FIG. 2A, since the bright part of the self-image of the phase grating G1 and the X-ray absorber G2b of the absorption grating G2 are overlapped by half, the amount of the X-ray that can pass through the absorption grating G2 becomes an intermediate value between the case of the state A and the case of the state C. Therefore, the signal intensity of the X-ray detected by the detection unit 2 becomes an intermediate value between the case of state A and the case of state C. Such changes in the signal intensity of the X-ray detected by the detection unit 2 occur in all pixels 30 (see FIG. 4) in an image.

At each pixel 30, in the intensity-modulated signal 20, the overlapping degree of the bright portion of the self-image of the phase grating G1 and the X-ray absorber G2b of the absorption grating G2 is repeated with the grating pitch d2 of the absorption grating G2 as one cycle. Therefore, as shown in FIG. 2B, it becomes a sine wave shape (periodic function). Therefore, in order to acquire the intensity-modulated signal 20, it is only necessary to step the absorption grating G2 by the grating pitch d2 of in the X direction. In this embodiment, an example is shown in which the absorption grating G2 is stepped eight times by (d2/8) in the X direction of the grating pitch d2. The intensity-modulated signal 20 is acquired for all the pixels 30 of the detection unit 2 by acquiring the X-ray image at each stepped position. In the following description, this intensity-modulated signal may be referred to as a "step curve". In addition, performing X-ray photographing while translating the absorption grating G2 in the direction of the grating pitch d2 as described above in order to acquire a step curve 20 may be referred to as "fringe scanning". Since the fringe scanning can be performed by changing the relative position between phase grating G1 and the absorption grating G2, the fringe scanning can also be performed by translating the phase grating G1 in the direction of the grating pitch d1.

Figure 3:
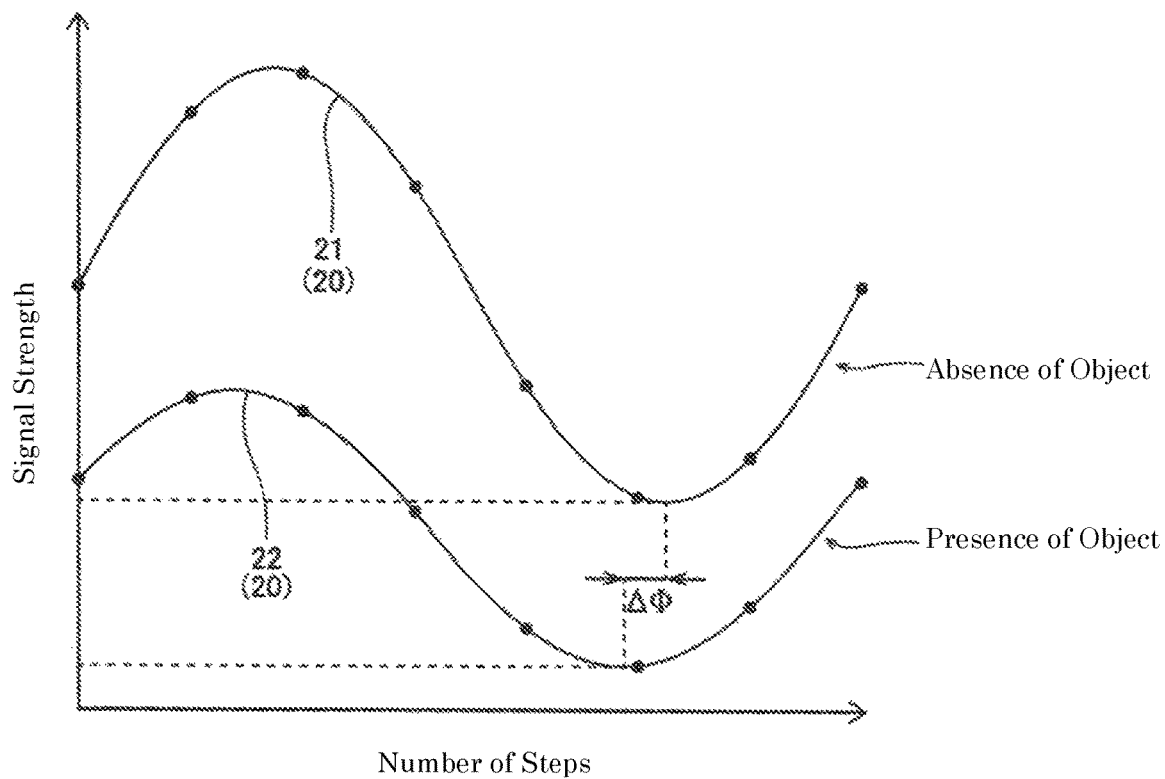
FIG. 3 is a diagram for explaining a phase-contrast between step curves due to the presence or absence of an object.

As shown in FIG. 3, the phase-contrast Δφ may occur in the step curve 20 between the case where X-ray photographing is performed by placing an object T between the phase grating G1 and the absorption grating G2 and the case where X-ray photographing is performed without placing an object T. This is because the self-image of the phase grating G1 is shifted due to refraction of the X-ray passing through the object T, so that the signal intensity of the X-ray detected by the detection unit 2 changes. The phase-contrast Δφ due to such an object T remarkably appears in the pixel 30 imaged the vicinity of the edge portion (outer surface or inner surface) of the object T in which the X-ray is refracted. With this, an X-ray phase-contrast image 42 based on the value of phase-contrast Δφ due to the object T can be generated.

Figure 4:
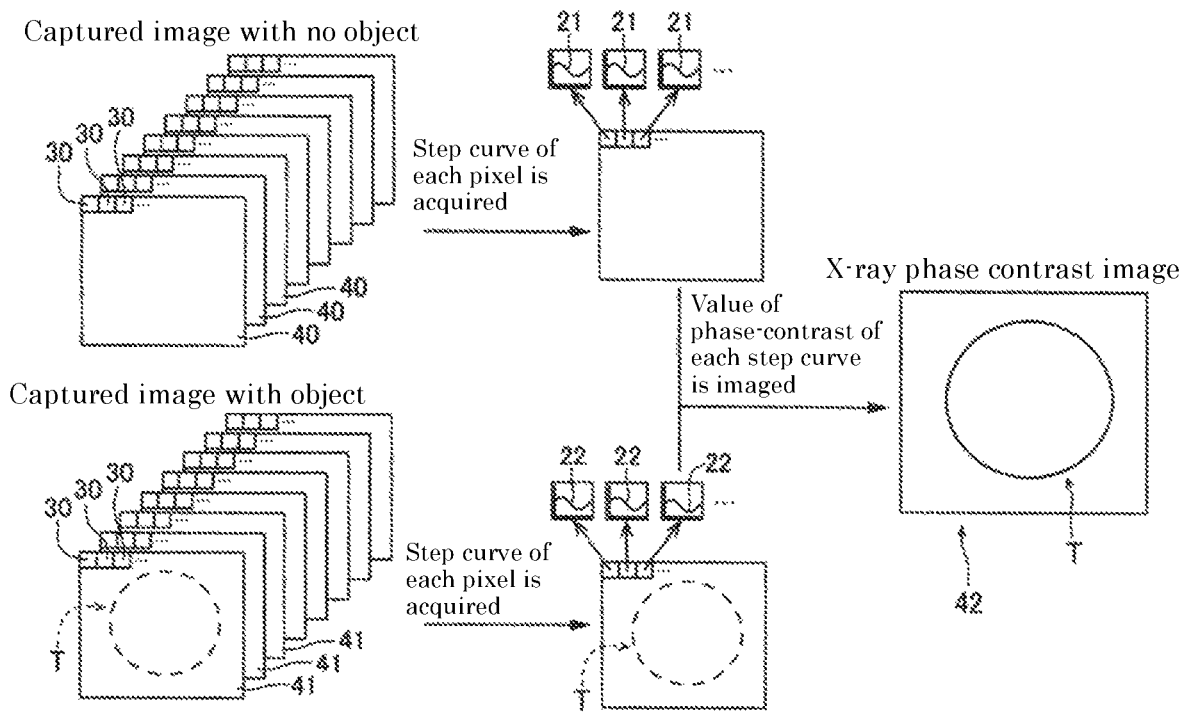
FIG. 4 is a diagram for explaining a generation method of an X-ray phase-contrast image.

Specifically, as shown in FIG. 4, X-ray photographing is performed while performing fringe scanning in the case where no object T is placed between the phase grating G1 and the absorption grating G2 and the case where an object T is placed therebetween. A captured image 40 when no object T is placed and a captured image 41 when an object T is placed are captured for at least one period of the grating pitch d2 of the absorption grating G2. The phase-contrast Δφ of the step curve 20 in the same pixel 30 is acquired by the captured image 40 in the case where no object T is placed and the captured image 41 in the case where an object T is placed. By imaging the value of this phase-contrast Δφ, an X-ray phase-contrast image 42 is generated. In the following description, the captured image 40 in the case where no object T is placed and the captured image 41 in the case where an object T is placed may sometimes be referred to as an "AIR image" and an "object captured image", respectively.

Figure 5:
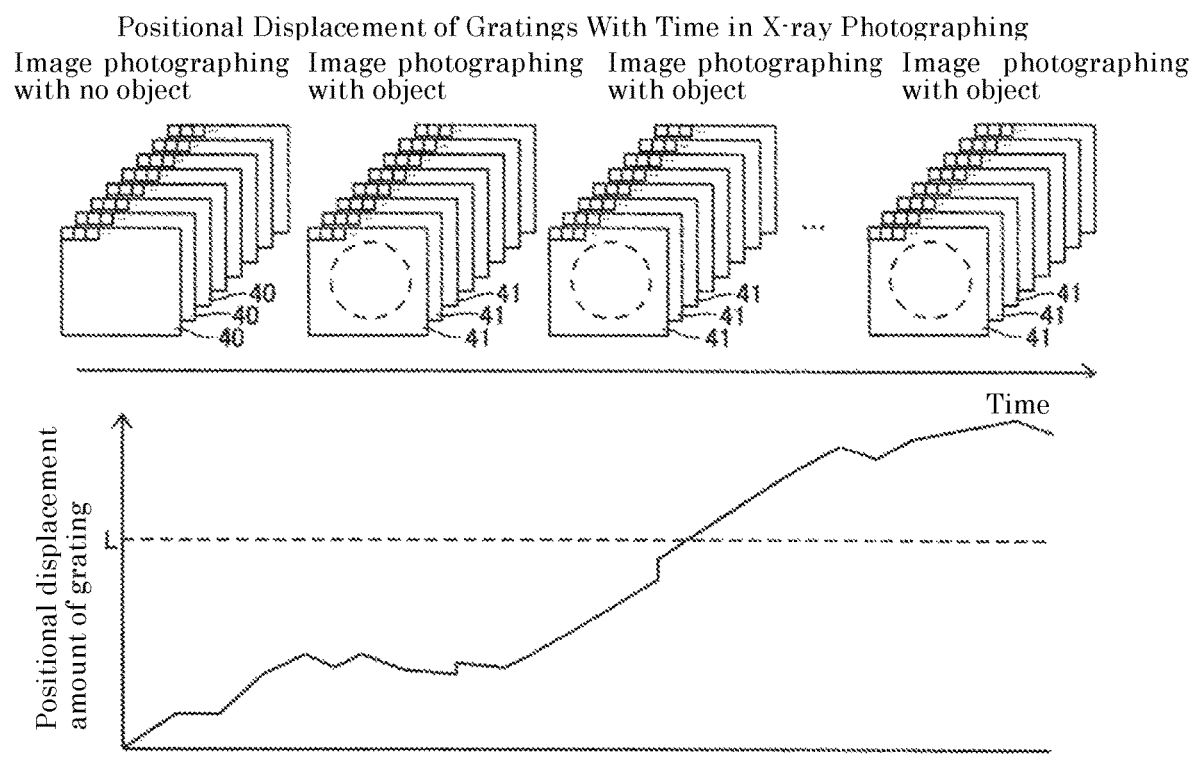
FIG. 5 is a diagram for explaining a displacement of relative positions of a plurality of gratings with time of X-ray photographing.

As shown in FIG. 5, in the X-ray photographing for generating an image including the X-ray phase-contrast image 42, first, an AIR image 40 is captured and then an object captured image 41 is repeatedly captured. In the meantime, with the lapse of time from the start of the X-ray photographing, the grating moving stages 4a and 4b supporting the phase grating G1 and the absorption grating G2 respectively cause expansion and contraction due to the influence of heat at around the grating moving stages 4a and 4b, so that grating may sometimes be displaced from the initial position. Here, the initial positions of the grating moving stages 4a and 4b are the positions of the grating moving stages 4a and 4b at the time of capturing the AIR image 40. When such displacements of initial positions of the grating moving stages 4a and 4b occur, as shown in FIG. 5, the phase-contrast Δφ between when acquiring the step curve 21 by the first AIR image 40 and when acquiring the step curve 22 by the object captured image 41 in the case where positional displacements from the initial positions occurred in the grating moving stages 4a and 4b with the lapse of time, becomes a state in which the phase-contrast ΔΦa due to the positional displacements from the initial positions of the grating moving stages 4a and 4b is added in addition to the phase-contrast ΔΦ due to the object T. That is, the phase-contrast Δφ between the step curve 21 by the AIR image 40 and the step curve 22 by the object captured image 41 is represented by (ΔΦ+ΔΦa).

The addition of the phase-contrast ΔΦ due to the positional displacements of the grating moving stages 4a and 4b from the initial position in the pitch direction equally appear over the entire image detected by the detection unit 2. Therefore, in the entire X-ray phase-contrast image 42, the step curves 21 and 22 become a state offset by the phase-contrast ΔΦa as compared with the absence of the positional displacement from the initial positions of the grating moving stages 4a and 4b.

This offset can be corrected during the process of generating the X-ray phase-contrast image 42. However, when the magnitude of this offset becomes, for example, close to the half cycle (π) of the phase of the step curve 22, in addition to the offset, the phase-contrast ΔΦ due to the object T is added near at the edge portion of the object T. Therefore, phase folding (phase wrapping) occurs in which the phase-contrast between the step curve 21 by the AIR image 40 and the step curve 22 by the object captured image 41 is folded within the range of 2π.

When this phase folding occurs, for example, even if the phase-contrast Δφ obtained by adding the phase-contrast ΔΦa offset to the phase-contrast ΔΦ due to the object T is (3/2)π, it becomes impossible to distinguish the phase-contrast from the case where the phase-contrast Δφ is −(½)π. As a result, the pixel 30 measured as an erroneous value becomes a state in which black and white are inverted.

In order to suppress the occurrence of this phase folding, the X-ray phase-contrast imaging apparatus 100 of this embodiment is configured to correct the positional displacements of the initial positions of the grating moving stages 4a and 4b.

(X-Ray Phase Contrast Image Correction Method)

Next, with reference to FIG. 6, a method of correcting the positional displacements of the initial positions of the grating moving stages 4a and 4b will be described.

In order to acquire the step curves 21 and 22 of each pixel 30 by the AIR image 40 and the object captured image 41, when X-ray photographing is performed by fringe scanning by steps of M times, the signal intensity of the X-ray detected by the detection unit 2 is expressed by the following equation (2).

$$I_k(x, y) = \sum_n a_n \exp\left(-2i\pi n\left(\frac{z_0}{d_1}\varphi_x(x, y) + \frac{k}{M}\right)\right) \quad (2)$$

Where, $I_k(x, y)$ is the signal intensity of the X-ray at the $k^{th}$ step in the pixel coordinate (x, y) and corresponds to the signal intensity shown in FIGS. 2 and 3.

When the signal intensity at each step k of each pixel 30 in the AIR image 40 is $I_{k0}(x, y)$, the signal intensity of each pixel 30 in the object captured image 41 is $I_k(x, y)$, and the following equations (3) and (4) are defined, the phase-contrast Δφ (x, y) at the pixel coordinate (x, y) is expressed by the following equation (5).

$$S(x, y) = \sum_{k=1}^{M} I_k(x, y)\exp\left(-\frac{2i\pi k}{M}\right) \quad (3)$$

$$S_0(x, y) = \sum_{k=1}^{M} I_{0k}(x, y)\exp\left(-\frac{2i\pi k}{M}\right) \quad (4)$$

$$\Delta\phi(x, y) = \frac{d1}{2\pi z_0}\arg\left[\frac{S(x, y)}{S_0(x, y)}\right] = \frac{d1}{2\pi z_0}(\arg[S(x, y)] - \arg[S_0(x, y)]) \quad (5)$$

Figure 6:
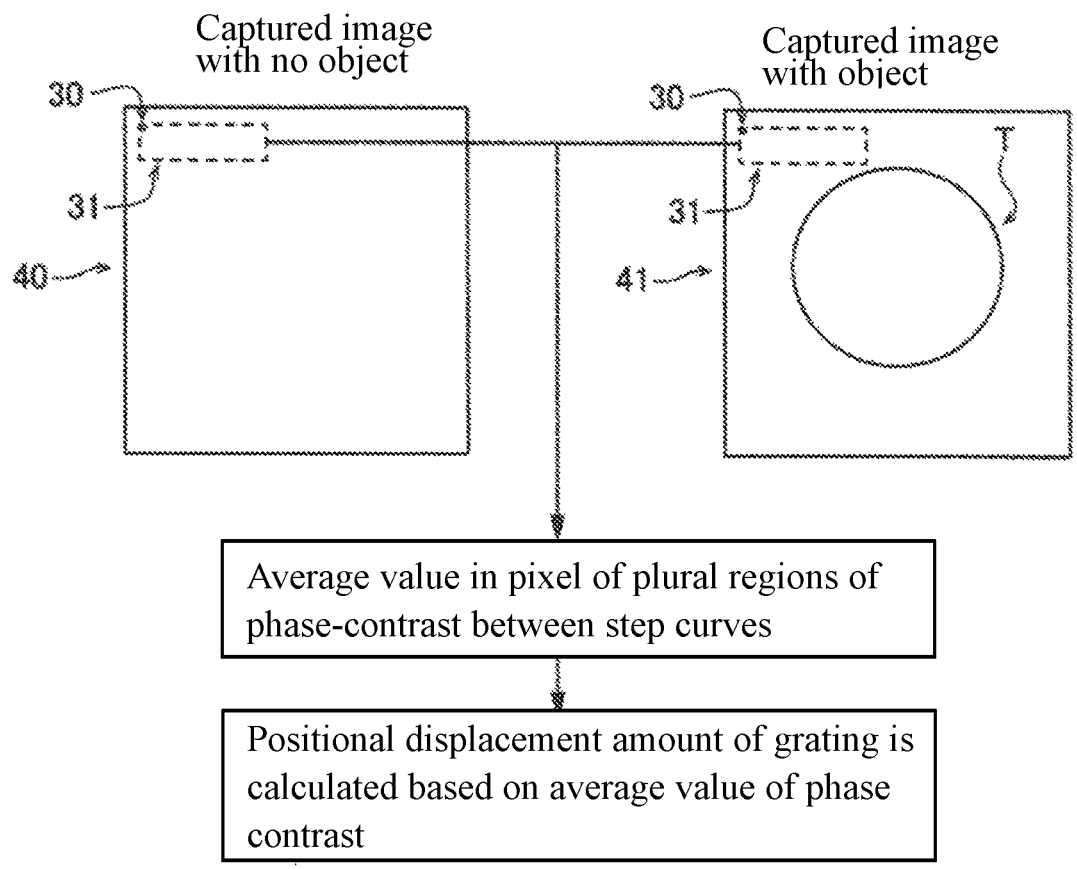
FIG. 6 is a diagram for explaining a method of calculating a displacement amount of relative positions of a plurality of gratings by a phase-contrast between step curves.

In the X-ray phase-contrast imaging apparatus 100 according to this embodiment, as shown in FIG. 6, the average value Mφ in the region 31 of the plurality of pixels in the AIR image 40 (or object captured image 41) of the phase-contrast Δφ between the step curve 21 by the AIR image 40 and the step curve 22 by the object captured image 41 is calculated. Based on this average value Mφ, the position of phase grating G1 or absorption grating G2 is corrected by the grating moving stages 4a and 4b. The displacement amount $\Delta D_1$ in the case of correcting the position of the phase grating G1 and the displacement amount $\Delta D_2$ in the case of correcting the position of the absorption grating G2 are represented by the following equations (6) and (7), respectively.

$$\Delta D_1 = d1\frac{M_\phi}{2\pi} \quad (6)$$

$$\Delta D_2 = d2\frac{M_\phi}{2\pi} \quad (7)$$

As described above, in order to calculate the displacement amount $\Delta D_1$ or $\Delta D_2$ from the initial position of the grating, in the X-ray phase-contrast imaging apparatus 100 of this embodiment, the average value $M\varphi$ in the region 31 of the plurality of pixels of the phase-contrast $\Delta\varphi$ is used. Also, as shown in FIG. 6, it is preferable not to include the object T in the AIR image 40 (or object captured image 41) in the region 31 of the plurality of pixels, but the object T may be included. In order to calculate the displacement amount $\Delta D_1$ or $\Delta D_2$, in place of the average value $M\varphi$ in the region 31 of the plurality of pixels of the phase-contrast $\Delta\varphi$, an intermediate value, etc., in the region 31 of the plurality of pixels of the phase-contrast $\Delta\varphi$ may be used.

In the X-ray phase-contrast imaging apparatus 100 according to this embodiment, it is configured such that, as shown in FIG. 5, a threshold value L is set to the displacement amount $\Delta D_1$ or $\Delta D_2$ from the respective initial position of the phase grating G1 or the absorption grating G2, and the displacement amount is corrected when the displacement amount $\Delta D_1$ or $\Delta D_2$ exceeds the threshold value L. The threshold value L is set to be smaller than $\pi 0$ so that the average value $M\varphi$ of the phase-contrast $\Delta\varphi$ in the region 31 of the plurality of pixels does not cause phase folding in the step curves 21 and 22. Further, for example, the threshold value L is set to be equal to or more than $(2/3)\pi$ so that the number of corrections of the positional displacement does not become too much.

Further, in the X-ray phase-contrast imaging apparatus 100 according to this embodiment, it is configured such that when fringe scanning is performed by the phase grating G1, a positional displacement of the phase grating G1 is corrected by the grating moving stage 4a and when fringe scanning is performed by the absorption grating G2, a positional displacement of the absorption grating G2 is corrected by the grating moving stage 4b.

Further, in the X-ray phase-contrast imaging apparatus 100 according to this embodiment, it is normally configured such that the displacement amount $\Delta D_1$ or $\Delta D_2$ is corrected by moving the absorption grating G2 having the largest grating pitch among gratings.

Figure 7:
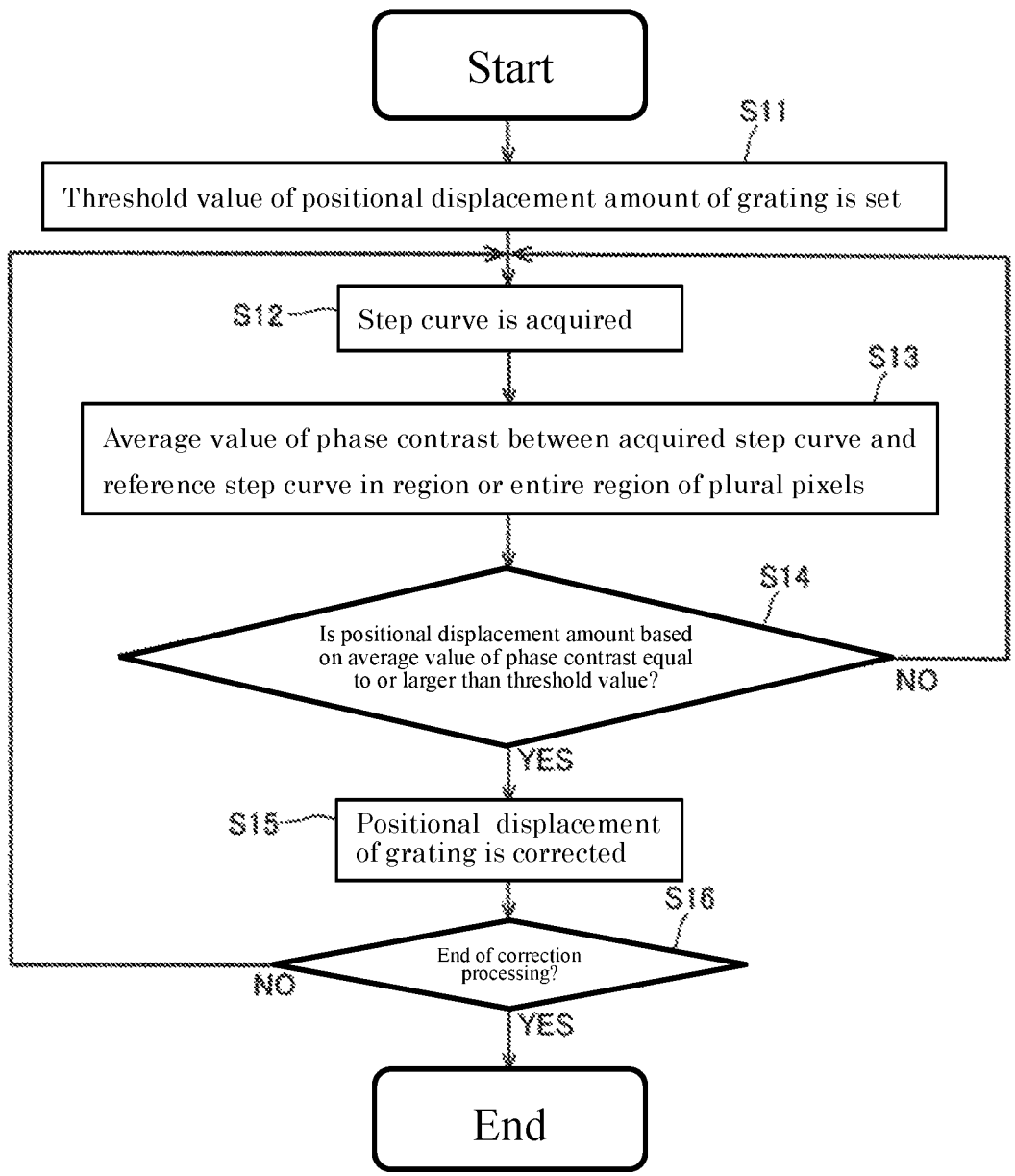
FIG. 7 is a flowchart of a process for correcting a displacement of relative positions of a plurality of gratings.

Next, with reference to FIG. 7, a flowchart of the correction processing of a positional displacement of the grating position in the X-ray phase-contrast imaging apparatus 100 will be described. The processing of the flowchart is performed by the control unit 3. It is assumed that the AIR image 40 is captured and the reference step curve 21 has been acquired.

First, in Step S11, the control unit 3 sets a threshold value L of the displacement amount $\Delta D_1$ or $\Delta D_2$ of relative positions of a plurality of gratings by the user's input or by reading the set values stored in a storage.

When the object captured image 41 is captured, the control unit 3 acquires a step curve 22 from the object captured image 41 in Step S12.

Next, in Step S13, the control unit 3 calculates the average value $M\varphi$ of the phase-contrast $\Delta\varphi$ between the acquired step curve 22 and the reference step curve 21 in the region 31 or the entire region of the plurality of pixels of the object captured image 41 (or AIR image 40).

Next, in Step S14, the control unit 3 calculates the displacement amount $\Delta D_1$ or $\Delta D_2$ of the relative positions of the plurality of gratings based on the average value $M\varphi$ of the phase-contrast $\Delta\varphi$ and judges whether or not the displacement amount $\Delta D_1$ or $\Delta D_2$ is larger than the threshold value L set in Step S11. In Step S14, when the displacement amount $\Delta D_1$ or $\Delta D_2$ is equal to or greater than the threshold value L, the process proceeds to Step S15. Further, in Step S14, when the displacement amount $\Delta D_1$ or $\Delta D_2$ is less than the threshold value L, the process returns to Step S12.

In Step S15, the control unit 3 corrects the positional displacements of the grating moving stage 4a or 4b by moving the grating moving stage 4a by the displacement amount $\Delta D_1$ or by moving the grating moving stage 4b by the displacement amount $\Delta D_2$.

Thereafter, in Step S16, it is determined whether to end the correction processing of the positional displacement of the grating position based on the instruction from the user, the termination of the X-ray photographing, etc. In Step S16, when the correction processing of the positional displacement at the grating position is terminated, the correction processing is terminated. Further, in Step S16, when the correction processing of the positional displacement of the grating position is not terminated, the process returns to Step S12.

(Effects of First Embodiment)

In the first embodiment, the following effects can be obtained.

In the first embodiment, as described above, it is configured such that the X-ray phase-contrast imaging apparatus 100 acquires the displacement amount $\Delta D_1$ or $\Delta D_2$ of relative positions of a plurality of gratings based on a plurality of step curves 20. As a result, even if a displacement occurs in the relative positions of the plurality of gratings, by appropriately correcting the displacement amount $\Delta D_1$ or $\Delta D_2$, the accumulation of the displacement amount $\Delta D_1$ or $\Delta D_2$ can be suppressed. As a result, by correcting the displacement amount $\Delta D_1$ or $\Delta D_2$ before the phase-contrast $\Delta\varphi$ between the plurality of step curves 20 approaches close to $\pi$, it is possible to suppress an occurrence of phase folding in the X-ray phase-contrast image 42 due to displacements of the plurality of relative positions.

Further, in the first embodiment, as described above, it is configured such that the X-ray phase-contrast imaging apparatus 100 acquires the displacement amount $\Delta D_1$ or $\Delta D_2$ based on the representative value obtained from the step curve 20 in the region 31 of the plurality of pixels detected by the detection unit 2 or the entire region thereof. Thus, for example, by acquiring the displacement amount $\Delta D_1$ or $\Delta D_2$ using the average value $M\varphi$, the median value, etc., of the phase-contrast $\Delta\varphi$ between the plurality of step curves 20 in the region 31 or the entire region of the plurality of pixels as a representative value, it is possible to acquire a displacement amount $\Delta D_1$ or $\Delta D_2$ with less error. As a result, it is possible to accurately correct the displacement amount $\Delta D_1$ or $\Delta D_2$.

Further, in the first embodiment, as described above, in the X-ray phase-contrast imaging apparatus 100, the region 31 of the plurality of pixels is preferably a region not including the edge portion of the object T. As a result, since it is not affected by the phase-contrast $\Delta\Phi$ due to the presence or absence of the object T, a displacement amount $\Delta D_1$ or $\Delta D_2$ with less error can be acquired. As a result, it is possible to more accurately correct the displacement amount $\Delta D_1$ or $\Delta D_2$.

Further, in the first embodiment, as described above, it is configured such that in the X-ray phase-contrast imaging apparatus 100, when the displacement amount $\Delta D_1$ or $\Delta D_2$ exceeds the preset threshold value L, the displacement amount $\Delta D_1$ or $\Delta D_2$ is corrected. With this, by setting the threshold value L of the displacement amount $\Delta D_1$ or $\Delta D_2$ so as not to cause phase folding, in the case where a displacement of the relative position is to the extent that phase folding does not occur, it becomes possible so that the displacement amount $\Delta D_1$ or $\Delta D_2$ is not corrected. As a result, it becomes unnecessary to correct the displacement amount $\Delta D_1$ or $\Delta D_2$ each time the step curve 22 is acquired, so that the number of corrections of the displacement amount $\Delta D_1$ or $\Delta D_2$ can be minimized.

In the first embodiment, as described above, the X-ray phase-contrast imaging apparatus 100 is provided with grating moving stages 4a and 4b to move at least any one of a plurality of gratings in order to change the intensity of the X-ray detected by the detection unit 2. This makes it possible to easily change the relative positions of the plurality of gratings.

Further, in the first embodiment, as described above, the X-ray phase-contrast imaging apparatus 100 is configured such that the displacement amount $\Delta D_1$ or $\Delta D_2$ is corrected by moving at least any one of the plurality of gratings by the grating moving stages 4a and 4b. With this, for example, when moving the gratings with the grating moving stages 4a and 4b to generate an X-ray phase-contrast image 42, a moving mechanism for generating the X-ray phase-contrast image 42 and a moving mechanism for correcting the displacement can be used in common. Therefore, the apparatus configuration can be simplified and the number of parts can be reduced.

Further, in the first embodiment, as described above, the X-ray phase-contrast imaging apparatus 100 is configured such that the displacement amount $\Delta D_1$ or $\Delta D_2$ is corrected by moving the grating having the maximum grating pitch among the plurality of gratings by the grating moving stages 4a and 4b. As a result, since the displacement amount $\Delta D_1$ or $\Delta D_2$ is proportional to the grating pitch, when correcting with a grating having a large grating pitch, compared with the case of correcting with a grating having a narrow grating pitch, the displacement amount $\Delta D_1$ or $\Delta D_2$ becomes large. As a result, since the distance by which the grating moving stages 4a and 4b are moved increases in order to correct the displacement amount $\Delta D_1$ or $\Delta D_2$, it is possible to easily correct the displacement amount $\Delta D_1$ or $\Delta D_2$.

Further, in the first embodiment, as described above, the X-ray phase-contrast imaging apparatus 100 is configured such that the displacement amount $\Delta D_1$ or $\Delta D_2$ is corrected by moving the grating moved to generate the X-ray phase-contrast image 42 among the plurality of gratings with the grating moving stages 4a and 4b. As a result, it is enough to move only a specific grating among a plurality of gratings, so the movement of the grating with the grating moving stages 4a and 4b can be performed easily.

Further, in the first embodiment, as described above, the X-ray phase-contrast imaging apparatus 100 is configured such that the imaging system 7 including the X-ray source 1, the plurality of gratings (phase grating G1, absorption grating G2) and the detection unit 2 and the object rotation stage 5 which relatively rotates the object T are further provided and that an tomographic image of the object T is acquired by relatively rotating the imaging system 7 and the object T with the object rotation stage 5. As a result, when acquiring a tomographic image of the object T, the acquiring time of the image becomes longer and a displacement of the grating relative position is likely to occur. Therefore, the X-ray phase-contrast imaging apparatus 100 capable of suppressing an occurrence of phase folding in the X-ray phase-contrast image 42 is preferable.

Second Embodiment

Figure 8:
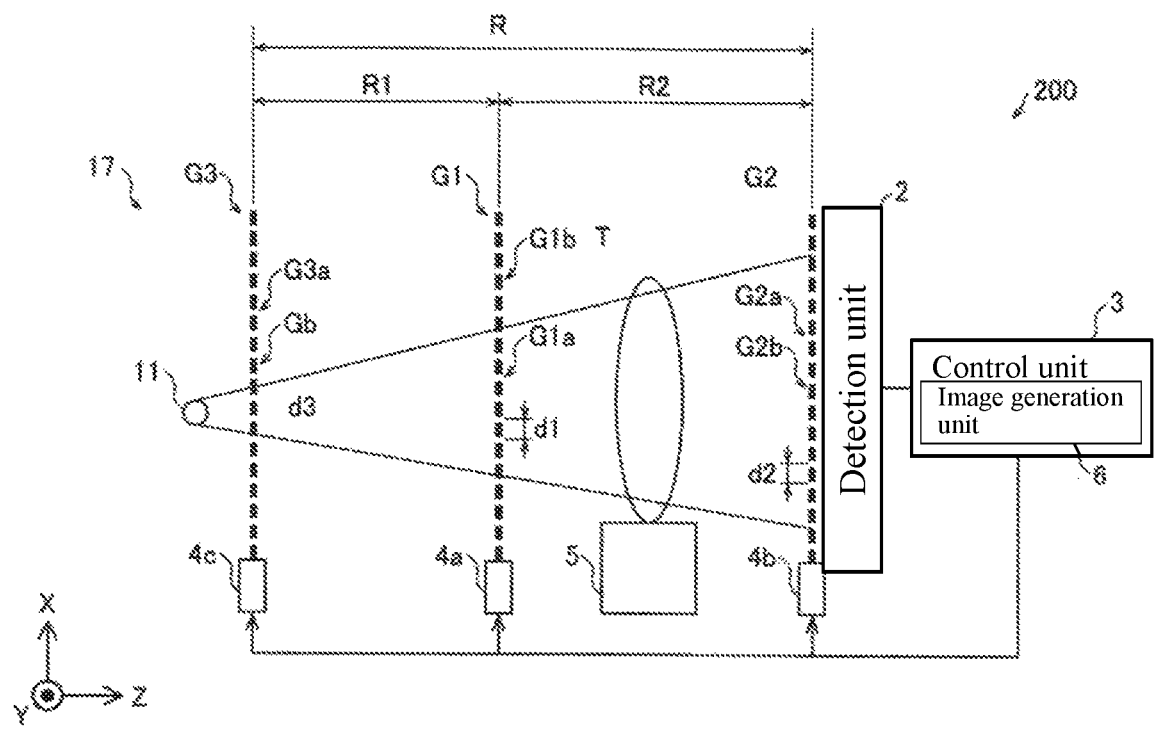
FIG. 8 is a diagram showing an overall configuration of an X-ray phase-contrast imaging apparatus according to a second embodiment of the present invention.

Next, a second embodiment will be described with reference to FIG. 8. In the second embodiment, in addition to the configuration of the first embodiment, a multi-slit G3 is further provided between the X-ray source 1 and the phase grating G1. The same configurations as those of the first embodiment are denoted by the same reference numerals in the drawings, and description thereof will be omitted.

(Configuration of X-Ray Phase Contrast Imaging Apparatus)

The X-ray phase-contrast imaging apparatus 200 according to the second embodiment of the present invention includes a multi slit G3 and a grating moving stage 4c in addition to the configuration of the X-ray phase-contrast imaging apparatus 100 of the first embodiment. Further, in the X-ray phase-contrast imaging apparatus 200, the X-ray source 11 is an X-ray source with higher power than the X-ray source 1 of the X-ray phase-contrast imaging apparatus 100 of the first embodiment. Note that the X-ray phase-contrast imaging apparatus 200 is an example of the "X-ray phase imaging apparatus" recited in claims. The multi slit G3 is an example of the "third grating" recited in claims. The grating moving stage 4c is an example of the "moving mechanism" recited in claims.

In the X-ray phase-contrast imaging apparatus 200, the X-ray source 11 is not required to be narrowed down the focus. Therefore, it is possible to irradiate an X-ray having X-ray intensity higher than that of the X-ray source 1 of the X-ray phase-contrast imaging apparatus 100 of the first embodiment. As a result, it is possible to shorten the time for extracting the X-ray phase-contrast image 42. Since the X-ray source 11 is large in the focus size, in order to form a self-image of the phase grating G1, it is necessary to micro-focus the X-ray to be irradiated.

The multi slit G3 is a grating capable of micro-focusing the X-ray irradiated from the X-ray source 1. The multi-slit G3 has a plurality of slits G3a and an X-ray absorber G3b arranged at a predetermined period (grating pitch d3) in the X direction. The slit G3a and X-ray absorber G3b are each formed so as to extend in the Y direction.

When the distance between the multi slit G3 and the phase grating G1 is R1, the distance between the phase grating G1 and the absorption grating G2 is R2, and the distance between the multi slit G3 and the absorption grating G2 is R (=R1+R2), the positional relationship with the phase grating G1, the absorption grating G2, the multi slit G3 is expressed by the following expression (8).

$$d3 = \frac{R1}{R2}d2 = \frac{R}{R2}d1 \qquad (8)$$

The grating moving stage 4c has a grating holding portion (not shown) for holding the multi slit G3. The grating moving stage 4c is configured to move the held multi slit G3 in a predetermined direction in the Z direction, the X direction, and the Y direction based on a signal sent from the control unit 3. The grating moving stage 4c is, for example, an electric positioning stage using a stepping motor or a piezo actuator. As a result, the relative position of the phase grating G1, the absorption grating G2, and the molality of slits G3 can be easily changed.

Based on the signal sent from the control unit 3, the object rotation stage 5 can rotate the object T with respect to the imaging system 17 including the X-ray source 11, the phase grating G1, the absorption grating G2, the multi slit G3, and the detection unit 2 about the X axis direction or the Y axis by 360 degrees.

Also in the configuration of the second embodiment, in the same manner as in the first embodiment, it is possible to perform fringe-scanning of any one of a plurality of grating steps. Also, in the same manner as in the first embodiment, by moving any one of the plurality of gratings, it is possible to correct displacements of relative positions of the plurality of gratings.

When the positional displacement of the relative position of phase grating G1, the absorption grating G2, and the plurality of slits G3 is corrected by moving the plurality of slits G3, the displacement amount $\Delta D_3$ of the relative position is expressed by the following equation (9).

$$\Delta D_3 = d3 \frac{M_\phi}{2\pi} \quad (9)$$

Other configurations of the second embodiment are the same as those of the first embodiment.

(Effects of the Second Embodiments)

In the second embodiment, the following effects can be obtained.

In the X-ray phase-contrast imaging apparatus 200 according to the second embodiment, as described above, in addition to the configuration of the X-ray phase-contrast imaging apparatus 100 according to the first embodiment, the plurality of gratings further includes a multi slit G3 provided between the X-ray source 11 and the phase grating G1. With this, by micro-focusing the X-ray irradiated from the X-ray source 11 using the multi slit G3, it becomes unnecessary to use an X-ray source 11 of micro-focus in order to form a self-image of the phase grating G1. Therefore, it becomes possible to use an X-ray source 11 with high X-ray intensity that cannot be obtained with an X-ray source 1 of micro-focus. As a result, the intensity of the X-ray irradiated from the X-ray source 11 is increased, and therefore the time for extracting the X-ray phase-contrast image 42 can be shortened.

Other effects of the second embodiment are the same as those of the first embodiment.

Modified Examples

It should be understood that the embodiments disclosed here are examples in all respects and are not restrictive. The scope of the present invention is shown by the scope of the claims rather than the descriptions of the embodiments described above, and includes all modifications (modified examples) within the meaning of equivalent and the scope of claims.

In the first and second embodiments, based on the step curve 21 of the AIR image 40, the displacement amounts of a plurality of grating relative positions are corrected based on the phase-contrast $\Delta \varphi$ with the step curve 22 of the object captured image 41, but the present invention is not limited to this. In the present invention, on the basis of the step curve 22 of the object captured image 41, the displacement amounts of a plurality of grating relative positions may be corrected based on the phase-contrast $\Delta \varphi$ of the step curve 22 of the object captured image 41 and the step curve 22 of the object captured image 41.

In the first and second embodiments, the capturing of the AIR image 40 is performed only once as the first one after the start of X-ray imaging as shown in FIG. 5, but the present invention is not limited thereto. In the present invention, the capturing of the AIR image 40 may be performed again. For example, the AIR image 40 and the object captured image 41 may be captured alternately, or the AIR image 40 may be captured every time the object captured image 41 is captured several times.

In the first and second embodiments, when the threshold value L is set to the displacement amount of the relative positions of the plurality of gratings and the threshold value L is exceeded, the displacement amount is corrected, but the present invention is limited to this. In the present invention, when the threshold value L is set as the time or the number of times of image capturing and the threshold value L is exceeded, the displacement amount may be corrected.

In the first and second embodiments, fringe scanning is performed by stepping any one grating among a plurality of gratings, but the present invention is not limited to this. In the present invention, it is possible to perform fringe scanning by simultaneously making a plurality of gratings step.

In the first and second embodiments, the displacement amount of a plurality of grating relative positions is corrected by the grating moved for fringe scanning among a plurality of gratings, but the present invention is not limited to this. In the present invention, by simultaneously moving a plurality of gratings, it is possible to correct the displacement amount of relative positions of a plurality of gratings.

In the first and second embodiments, the grating provided for forming the self-image by the Talbot effect is set as the phase grating G1, but the present invention is not limited thereto. In the present invention, it is enough that the self-image of the grating G1 is a stripe pattern, so the shadow of the grating G1 may be used as the stripe pattern of the self-image by using the absorption grating for the grating G1.

In the first and second embodiments, the object rotation stage 5 that rotates the object T and the imaging system relative to each other is provided, but the present invention is not limited thereto. In the present invention, it may be configured such that the object rotation stage 5 is omitted.

Further, in the first and second embodiments, the object T is placed on the downstream side (detector side) of the phase grating G1, but the present invention is not limited thereto. In the present invention, the object T may be on the upstream side (tube side) of the phase grating G1.

In the first and second embodiments, the displacement amounts of the relative positions of a plurality of gratings is acquired based on the representative values acquired from the step curve 20 in the region 31 of the plural pixels or the entire region thereof. However, the present invention is not limited to this. In the present invention, based on the phase-contrast $\Delta \varphi$ of a single pixel 30 itself, the displacement amount of the relative position of a plurality of gratings may be acquired.

In addition, in the aforementioned embodiment, for the sake of convenience of explanation, the description has been made using the flow driven type flow in which the processing of the control unit is sequentially performed along the processing flow, but the present invention is not limited thereto. In the present invention, the processing of the control unit may be performed by an event driven type (event driven type) processing that executes processing in units of events. In this case, it may be performed in a completely event driven manner, or a combination of event driving and flow driving may be performed.

In each of the aforementioned embodiments, other than the phase differential image, an image may be generated by using a dark field image, an absorption image, or an arbitrary combination of two or more images among these three images. Also, a non-interferometer may be used instead of Talbot interference. In that case, absorption grating is used instead of phase grating for the G2 grating.

The invention claimed is:

1. An X-ray phase imaging apparatus comprising:
an X-ray source;
a plurality of gratings including at least a first grating to which an X-ray from the X-ray source is irradiated and a second grating to which the X-ray that passed through the first grating is irradiated;
a detection unit configured to detect the X-ray that passed through the second grating;
an image generation unit configured to generate an image based on a phase-contrast between a first intensity-modulated signal representing an intensity change of the X-ray detected by the detection unit when an object is placed between the X-ray source and the first grating or between the first grating and the second grating and a second intensity-modulated signal when the object is not disposed therebetween; and
a control unit configured to acquire a displacement amount of a relative position of at least two gratings of the plurality of gratings based on the first and second intensity-modulated signals, to determine whether the displacement amount exceeds a preset threshold value, and to adjust the relative position of the at least two gratings in response to determining that the displacement amount exceeds the preset threshold value,
wherein the detection unit comprises a plurality of pixels, and
wherein preset threshold value is set to a value corresponding to a phase-contrast smaller than $\pi$ with respect to at least one of:
a single pixel of the detection unit,
a sub-region of the plurality of pixels of the detection unit, and
the entire region of the plurality of pixels.

2. The X-ray phase imaging apparatus according to claim 1,
wherein the displacement amount is obtained based on a representative value obtained from the first and second intensity-modulated signals of a plurality of pixels of the detection unit.

3. The X-ray phase imaging apparatus according to claim 2,
wherein the plurality of pixels of the detection unit are in a region of the detection unit that does not include an edge portion of the object.

4. The X-ray phase imaging apparatus according to claim 1,
wherein the X-ray phase imaging apparatus further comprises a moving mechanism configured to move at least one of the plurality of gratings to correct the displacement amount in response to a determination by the control unit that the displacement amount exceeds the preset threshold value.

5. The X-ray phase imaging apparatus according to claim 1,
wherein the plurality of gratings further includes a third grating provided between the X-ray source and the first grating.

6. The X-ray phase imaging apparatus according to claim 1, further comprising
a moving mechanism configured to move at least one of the plurality of gratings to change an intensity of the X-ray detected by the detection unit.

7. The X-ray phase imaging apparatus according to claim 6,
wherein the moving mechanism is configured to move at least one of the plurality of gratings to correct the displacement amount.

8. The X-ray phase imaging apparatus according to claim 6,
wherein the moving mechanism is configured to correct the displacement amount by moving the grating having a maximum grating pitch among the plurality of gratings.

9. The X-ray phase imaging apparatus according to claim 6,
wherein the moving mechanism is configured to move at least a first grating of the plurality of gratings in a stepwise fashion to generate the first intensity-modulated signal and the second intensity-modulated signal as part of generating the image by the image generation unit, and
wherein the moving mechanism is configured to correct the displacement amount by moving the first grating.

10. The X-ray phase imaging apparatus according to claim 1, further comprising
a rotation mechanism configured to relatively rotate an imaging system and the object, the imaging system including the X-ray source, the plurality of gratings, and the detection unit,
wherein the rotation mechanism is configured to capture a tomographic image of the object by relative rotating the imaging system and the object.

11. The X-ray phase imaging apparatus according to claim 1,
wherein preset threshold value is set to a value corresponding to a phase-contrast smaller than $\pi$ and equal to or more than $(\tfrac{2}{3})\pi$ with respect to at least one of:
a single pixel of the detection unit,
a sub-region of the plurality of pixels of the detection unit, and
the entire region of the plurality of pixels.

* * * * *